United States Patent [19]

Hoehn

[11] 4,218,461
[45] Aug. 19, 1980

[54] 2,3-DIHYDRO-2-[(1H-IMIDAZOL-1-YL)-METHYLENE]-1H-INDEN-1-ONES

[75] Inventor: Hans Hoehn, Tegernheim, Fed. Rep. of Germany

[73] Assignee: E. R. Squibb & Sons, Inc., Princeton, N.J.

[21] Appl. No.: 66,726

[22] Filed: Aug. 15, 1979

[51] Int. Cl.$^2$ .................. A61K 31/415; C07D 233/56
[52] U.S. Cl. .................. 424/273 R; 542/428
[58] Field of Search .................. 548/335; 424/273 R; 542/428

[56] References Cited

U.S. PATENT DOCUMENTS

| | | | |
|---|---|---|---|
| 3,255,201 | 6/1966 | Beaman et al. | 548/338 |
| 3,454,565 | 7/1969 | Safir et al. | 542/428 |
| 3,728,340 | 4/1973 | Raabe et al. | 542/428 |
| 3,772,282 | 11/1973 | Ford et al. | 542/428 |
| 3,991,201 | 11/1976 | Heeres et al. | 424/273 R |
| 4,006,243 | 2/1977 | Strehlke et al. | 548/335 |
| 4,115,578 | 9/1978 | Miller et al. | 548/335 |
| 4,118,461 | 10/1978 | Miller et al. | 548/335 |

FOREIGN PATENT DOCUMENTS 49-12406  3/1974  Japan ...................... 548/335

OTHER PUBLICATIONS

Gupta et al.: Indian Jour. of Chem. vol. 15B, Jul. 1977, pp. 641–644.

*Primary Examiner*—Henry R. Jiles
*Assistant Examiner*—Jane T. Fan
*Attorney, Agent, or Firm*—Lawrence S. Levinson; Burton Rodney

[57] ABSTRACT

New 2,3-dihydro-2-[(1H-imidazol-1-yl)-methylene]-1H-inden-1-ones are provided having the general formula

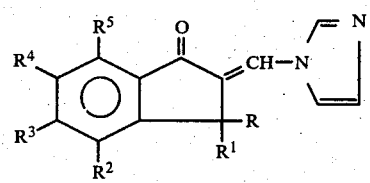

wherein
R, $R^1$, $R^2$, $R^3$, $R^4$ and $R^5$ may be the same or different and each is hydrogen, lower alkyl, halogen, lower alkoxy, lower alkylthio, phenyl-lower alkyl, phenyl or substituted phenyl.

The above compounds and their salts are useful as antifungal and antibacterial agents.

14 Claims, No Drawings

2,3-DIHYDRO-2-[(1H-IMIDAZOL-1-YL)-METHYLENE]-1H-INDEN-1-ONES

SUMMARY OF THE INVENTION

This invention relates to new 2,3-dihydro-2-[(1H-imidazol-1-yl) methylene]-1H-inden-1-ones and the acid addition salts of these compounds having the general formula

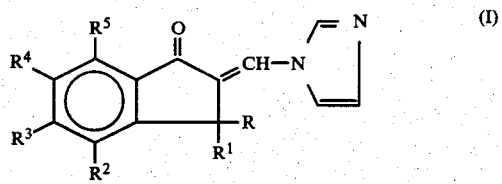

The symbols R, $R^1$, $R^2$, $R^3$, $R^4$ and $R^5$ have the following meaning in formula I and throughout the specification.

R, $R^1$, $R^2$, $R^3$, $R^4$ and $R^5$ may be the same or different and are hydrogen, lower alkyl, phenyl-lower alkyl, halogen, lower alkoxy, lower alkylthio, phenyl or substituted phenyl wherein the phenyl groups bears one halogen, hydroxy, lower alkoxy, lower alkyl, lower alkylthio, cyano or nitro group.

The new compounds of formula I and their salts are useful as antifungal and antibacterial agents.

DETAILED DESCRIPTION OF THE INVENTION

In formula I the lower alkyl groups include straight or branched chain hydrocarbon groups containing 1 to 7 carbon atoms. Examples of the type of groups contemplated are methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio. In all of these radicals the $C_1$–$C_4$, especially the $C_1$–$C_2$ members, are preferred.

The halogens are the four common halogens, chlorine and bromine being preferred in that order.

The substituted phenyl groups refer to phenyl rings bearing one of the simple substituents named, which are of the same character as described above. Unsubstituted phenyl is preferred.

Preferred embodiments of the invention are compounds of formula I wherein one of R and $R^1$ is hydrogen and the other is hydrogen, lower alkyl, such as methyl, phenyl, or mono- or di-halo-phenyl, wherein halo is preferably chloro, and $R^2$ and/or $R^4$ are hydrogen or halo, such as chloro, and $R^3$ and $R^5$ are hydrogen.

DESCRIPTION OF THE INVENTION

The new compounds of formula I are formed by the following series of reactions.

A 2,3-dihydro-1H-inden-4-one of the formula

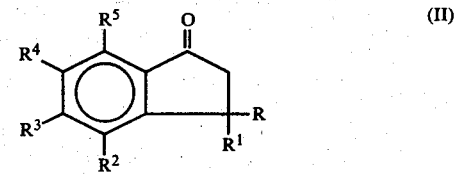

is made to react with alkyl formate of the formula

at room or elevated temperature in the presence of a condensing agent, e.g., metal alcoholate. The resulting compound of the formula

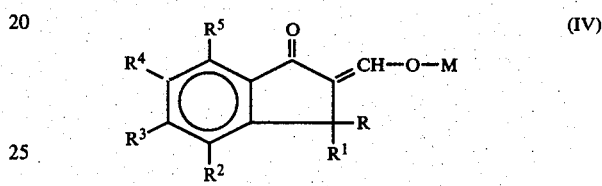

in which M represents metals like sodium, potassium or the like, is neutralized and then reacted with imidazole of the formula

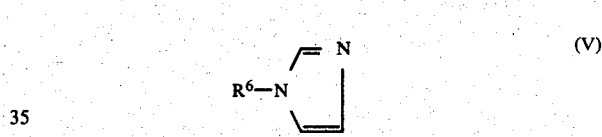

in which $R^6$ represents hydrogen, metals like sodium, potassium or the like, or carbonylimidazole or thionylimidazole, to give compounds of formula I.

A preferred method for preparing products of formula I is the reaction of the hydroxymethylene compound of formula IV (M=H) with the carbonyl-bis-imidazole or the thionyl-bis-imidazole of the formula

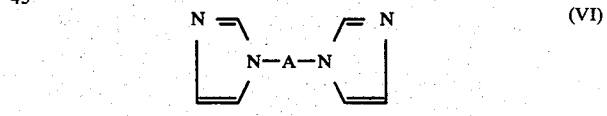

wherein A represents —CO— or —SO—.

Additional experimental details are found in the illustrative examples below.

The compounds of formula I form salts which are also part of this invention. The salts include acid addition salts, particularly the non-toxic, physiologically acceptable members. The compounds of formula I form salts by reaction with a variety of inorganic and organic acids providing acid addition salts including for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluene-sulfonate. The acid addition salts frequently provide a convenient means for isolating the product, e.g., by forming and precipitating the salt in the appropriate medium in which the salt is insoluble, then after separation of the salt, neutralizing with a base, such as barium hydroxide or sodium hydroxide, to obtain the free base of formula I. Other salts may then be formed from the free base by reaction with an equivalent of acid having the desired anion.

The new compounds of formula I and their salts are useful as antimicrobial agents, particularly as antifungal agents, and can be used to combat infections in various mammalian species, such as mice, rats, dogs, guinea pigs and the like, due particularly to organisms such as *Candida albicans* as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg/kg/day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc. as called for by accepted pharmaceutical practice. Preferably they are applied topically, e.g., intravaginally in a lotion or in a conventional cream base at a concentration of about 0.01 to 3 percent by weight for a period of 3 to 7 days, 2 to 4 times daily.

The following examples are illustrative of the invention. They represent particularly preferred embodiments and also serve as models for the preparation of other members of the group. All temperatures are on the Celsius scale.

EXAMPLE 1

2,3-Dihydro-2-[(1H-imidazol-1-yl)methylene]-1H-inden-1-one

A. 2,3-Dihydro-2-(hydroxymethylene)-1H-inden-1-one

The above starting material is prepared according to W. S. Johnson, J. M. Anderson and W. E. Shelberg, J. of the Am. Chem. Soc., Vol. 66, 218–222 (1944) and Vol. 67, 1745–1754 (1945). A quite similar procedure is described by P. Schenone, G. Bignardi (a) and S. Morasso, J. Heterocyclic Chem. 9, 1345 (1972). M.p. 110°–112° C., yield 71%.

B.

2,3-Dihydro-2-[(1H-imidazol-1-yl)-methylene]-1H-inden-1-one 9.6 G of 2,3-dihydro-2-(hydroxymethylene)-1H-inden-1-one (0.06 mol) are suspended in 150 ml of benzene. While stirring 11.5 g of carbonyl-bis-imidazole (0.072 mol) are added and the reaction mixture is warmed to about 70°–75° C. for a short time to get the components dissolved. If required, the solution is filtered clear and then allowed to stand at room temperature for 17 hours. The crystallized product is filtered off, washed with benzene and dried. Treatment with 100 ml of water and drying in the desiccator over $P_2O_5$ furnishes the 2,3-dihydro-2-[(1H-imidazol-1-yl)-methylene]-1H-inden-1-one which after recrystallization from ethylacetate melts at 183°–185° C., yield 10 g (79%).

EXAMPLE 2

2,3-Dihydro-2-[(1H-imidazol-1-yl)methylene]-3-phenyl-1H-inden-1-one

A.

2,3-Dihydro-2-(hydroxymethylene)-3-phenyl-1H-inden-1-one

The above starting material is prepared using the literature method mentioned in Example 1A; the said starting material melts at 135°–137° C. (ethyl acetate). Yield 92%.

B.

2,3-Dihydro-2-[(1H-imidazol-1-yl)-methylene]-3-phenyl-1H-inden-1-one

Following the procedure according to Example 1B, except reacting 2,3-dihydro-2-(hydroxymethylene)-3-phenyl-1H-inden-1-one with carbonyl-bis-imidazole, the title compound is produced, m.p. 204°–206° C. (ethanol); yield 72%.

EXAMPLE 3

6-Chloro-3-(4-chlorophenyl)-2,3-dihydro-2-[(1H-imidazol-1-yl)methylene]-1H-inden-1-one

A.

6-Chloro-3-(4-chlorophenyl)-2,3-dihydro-2-(hydroxymethylene)-1H-inden-1-one

The above starting material is prepared according to the literature method of Example 1A, m.p. 122°–124° C. (absolute ethanol), yield 89%.

B.

6-Chloro-3-(4-chlorophenyl)-2,3-dihydro-2-[(1H-imidazol-1-yl)methylene]-1H-inden-1-one Following the procedure according to the method of Example 1B, except reacting 6-chloro-3-(4-chlorophenyl)-2,3-dihydro-2-(hydroxymethylene)-1H-inden-1-one with carbonyl-bis-imidazole, the title compound is produced, m.p. 204°–205° C. (absolute ethanol); yield 63%.

EXAMPLE 4

4,6-Dichloro-3-(2,4-dichlorophenyl)-2,3-dihydro-2-[(1H-imidazol-1-yl)methylene]-1H-inden-1-one

A.

4,6-Dichloro-3-(2,4-dichlorophenyl)-2,3-dihydro-2-(hydroxymethylene)-1H-inden-1-one The above starting material is prepared following the procedure of Example 1A, m.p. 189°–191° C. (ethylacetate); yield 75%.

B.

4,6-Dichloro-3-(2,4-dichlorophenyl)-2,3-dihydro-2-[(1H-imidazol-1-yl)-methylene]-1H-inden-1-one 11.2 g of 4,6-dichloro-3-(2,4-dichlorophenyl)-2,3-dihydro-2-(hydroxymethylene)-1H-inden-1-one (0.03 mol) are suspended in 150 ml of benzene. After addition of 5.4 g of carbonyl-bis-imidazole (0.033 mol) both reaction components dissolve at room temperature. Stirring is continued at room temperature for about 2 hours. The precipitated product is worked up as described in Example 1B, m.p. 194°–196° C. (absolute ethanol); yield 5.9 g. An additional crop of 4.0 g (m.p. 193°–195° C.) is obtained by evaporation of the mother liquor and treatment of the residual product with water and ether. Total yield 9.9 g (78%).

EXAMPLES 5 to 24

The following additional compounds shown in Column II of Table A set out below are produced by the procedure of Example 1, by substituting for 2,3-dihydro-2-(hydroxymethylene)-1H-inden-1-one the compound shown in Column I of Table A below.

TABLE A

| | Column I | | | | | | Column II | | | | | |
|---|---|---|---|---|---|---|---|---|---|---|---|---|
| Ex. No. | R | $R^1$ | $R^2$ | $R^3$ | $R^4$ | $R^5$ | R | $R^1$ | $R^2$ | $R^3$ | $R^4$ | $R^5$ |
| 5 | $CH_3$ | H | H | H | H | H | | | | | | |
| 6. | H | H | Cl | H | $C_2H_5$ | H | | | as in Column I | | | |
| 7. | H | H | H | H | Cl | H | | | | | | |
| 8. | H | H | $CH_3$ | H | $CH_3$ | H | | | | | | |
| 9. | $C_2H_5$ | Br | $CH_3O$ | H | $CH_3O$ | H | | | | | | |
| 10. | $CH_3O$ | H | H | Cl | H | H | | | | | | |
| 11. | $CH_3S$ | Cl | H | H | H | Br | | | | | | |
| 12. | $C_6H_5CH_2$ | Br | H | $C_2H_5$ | $C_2H_5$ | $C_2H_5$ | | | | | | |
| 13. | p-OH—$C_6H_4$ | H | H | H | $C_2H_5$ | H | | | | | | |
| 14. | o-$CH_3$—$C_6H_4$ | H | H | H | Br | Br | | | | | | |
| 15. | m-$C_2H_5O$—$C_6H_4$ | Br | H | H | H | $CH_3$ | | | | | | |
| 16. | p-$CH_2S$—$C_6H_4$ | Cl | H | H | Cl | Cl | | | | | | |
| 17. | o-CN—$C_6H_4$ | H | H | H | Br | Br | | | | | | |
| 18. | p-$NO_2$—$C_6H_4$ | H | H | H | H | $C_6H_5$ | | | | | | |
| 19. | $C_2H_5OC_2H_4$ | Cl | H | H | $C_3H_7S$ | H | | | | | | |
| 20. | $C_6H_5OC_2H_4$ | Br | $CH_3$ | $C_2H_5O$ | H | H | | | | | | |
| 21. | $C_6H_5C_2H_4$ | H | H | $C_6H_5$ | $C_6H_5$ | H | | | | | | |
| 22. | $C_6H_5$ | H | $CH_3O$ | H | Cl | H | | | | | | |
| 23. | H | Cl | H | H | $C_2H_5S$ | H | | | | | | |
| 24. | H | H | H | H | $C_6H_5CH_2$ | H | | | | | | |

What is claimed is:
1. A compound of the formula

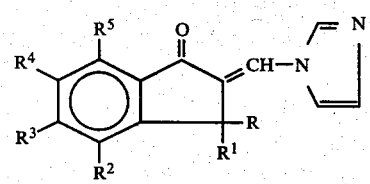

wherein
R, $R_1$, $R^2$, $R^3$, $R^4$ and $R^5$ may be the same or different and each is hydrogen, lower alkyl, halogen, lower alkoxy, lower alkylthio, phenyl-lower alkyl, phenyl or substituted phenyl, wherein the phenyl bears one halogen, hydroxy, lower alkoxy, lower alkyl, lower alkylthio, cyano or nitro group;
and non-toxic physiologically acceptable acid addition salts thereof.

2. The compound as defined in claim 1 wherein R and $R^1$ are hydrogen.

3. The compound as defined in claim 1 wherein one of R and $R^1$ is lower alkyl, phenyl, or phenyl containing one or two halo substituents and the other is hydrogen.

4. The compound as defined in claim 3 wherein one of $R^2$, $R^3$, $R^4$ and $R^5$ is chlorine and the remainder hydrogen.

5. The compound as defined in claim 1 in the form of its hydrochloride salt.

6. The compound as defined in claim 1 having the name 2,3-dihydro-2-[(1H-imidazol-1-yl)methylene]-1H-inden-1-one or its hydrochloride salt.

7. The compound as defined in claim 1 having the name 6-chloro-2,3-dihydro-2-(1H-imidazol-1-ylmethylene)-1H-inden-1-one.

8. The compound as defined in claim 1 having the name 2,3-dihydro-2-(1H-imidazol-1-ylmethylene)-3-phenyl-1H-inden-1-one.

9. The compound as defined in claim 1 having the name 6-chloro-3-(4-chlorophenyl)-2,3-dihydro-2-(1H-imidazol-1-ylmethylene)-1H-inden-1-one.

10. The compound as defined in claim 1 having the name 4,6-dichloro-3-(2,4-dichlorophenyl)-2,3-dihydro-2-(1H-imidazol-1-ylmethylene)-1H-inden-1-one.

11. The compound as defined in claim 1 having the name 2,3-dihydro-2-(1H-imidazol-1-ylmethylene)-3-methyl-1H-inden-1-one.

12. The compound as defined in claim 1 having the name 4-chloro-2,3-dihydro-2-(1H-imidazol-1-ylmethylene)-1H-inden-1-one.

13. An antimicrobial composition comprising an effective amount of a compound as defined in claim 1 and a pharmaceutically acceptable carrier therefor.

14. A method for treating bacterial or fungal infections in mammals which comprises administering to a mammalian host an effective amount of a compound as defined in claim 1.

* * * * *

UNITED STATES PATENT AND TRADEMARK OFFICE
CERTIFICATE OF CORRECTION

PATENT NO. : 4,218,461
DATED : August 19, 1980
INVENTOR(S) : Hans Hoehn

It is certified that error appears in the above-identified patent and that said Letters Patent are hereby corrected as shown below:

Column 6, Table A, Column II, under headings "$R$  $R^1$  $R^2$  $R^3$  $R^4$  $R^5$" insert --⏝--.

Column 5, line 57, "$R_1$" should read --$R^1$--.

Signed and Sealed this

Sixth Day of January 1981

[SEAL]

Attest:

SIDNEY A. DIAMOND

Attesting Officer

Commissioner of Patents and Trademarks